US006733999B2

(12) United States Patent
Cruz-Perez et al.

(10) Patent No.: US 6,733,999 B2
(45) Date of Patent: May 11, 2004

(54) **METHOD FOR DETECTION OF *STACHYBOTRYS CHARTARUM* IN PURE CULTURE AND FIELD SAMPLES USING QUANTITATIVE POLYMERASE CHAIN REACTION**

(75) Inventors: Patricia Cruz-Perez, Las Vegas, NV (US); Mark P. Buttner, Henderson, NV (US)

(73) Assignee: University of Nevada, Las Vegas, NV (US)

( * ) Notice: Subject to any disclaimer, the term of this patent is extended or adjusted under 35 U.S.C. 154(b) by 0 days.

(21) Appl. No.: 10/080,959

(22) Filed: Feb. 22, 2002

(65) Prior Publication Data

US 2003/0054369 A1 Mar. 20, 2003

Related U.S. Application Data

(60) Provisional application No. 60/280,712, filed on Mar. 29, 2001.

(51) Int. Cl.$^7$ ............................ C12P 19/34; C12Q 1/68; C12Q 1/00; C12Q 1/04; C07H 21/04

(52) U.S. Cl. .................... 435/91.2; 435/91.1; 435/6; 435/34; 435/4; 536/23.1; 536/24.33

(58) Field of Search .............................. 435/91.2, 6, 4, 435/34, 91.1, 91.21; 536/24.33, 24.3, 23.1

(56) References Cited

U.S. PATENT DOCUMENTS 6,387,652 B1 * 5/2002 Haugland et al. ............... 435/34

FOREIGN PATENT DOCUMENTS

WO   WO 01/96612 A    12/2001
WO   WO 01/96612 A2 * 12/2001

OTHER PUBLICATIONS

Alvarez, A.J., Buttner, M.P., Toranzos, G.A. et al. (1994). The use of solid–phase polymerase chain reaction for the enhanced detection of airborne microorganisms. Applied and Environmental Microbiology 60, 374–376.

Alvarez, A.J., Buttner, M.P. & Stetzenbach, L.D. (1995). PCR for bioaerosol monitoring: sensitivity and environmental interference. Applied and Environmental Microbiology 61, 3639–3644.

Sawyer, M.H., Chamberlin, C.J., Wu, Y.N., Aintablian, N., & Wallace, M.R. (1994). Detection of varicella–zoster virus DNA in air samples from hospital rooms. Journal of Infectious Disease 169, 91–94.

Haugland, R.A., Vesper, S.J. & Wymer, L.J. (1999). Quantitative measurement of *Stachybotrys chartarum* conidia using real time detection of PCR products with the TaqMan™ fluorogenic probe system. Molecular and Cellular Probes 13, 329–340.

Leenders, A.C.A.P., Van Belkum, A., Behrendt, M., Luijendijk, A. & Verbrugh, H.A. (1999). Density and molecular epidemiology of Aspergillus in air and relationship to outbreaks of Aspergillus infection. Journal of Clinical Microbiology 37, 1752–1757.

Vesper, S., Dearborn, D.G., Yike, I. et al. (2000). Evaluation of *Stachybotrys chartarum* in the house of an infant with pulmonary hemorrhage: quantitative assessment before, during, and after remediation. Journal of Urban Health 77, 68–84.

Heid, C.A., Stevens, J., Livak, K.J. & Williams, P.M. (1996). Real time quantitative PCR. Genome Research 6, 986–994.

Haugland, R.A. & Heckman, J.L. (1998). Identification of putative sequence specific PCR primers for detection of the toxigenic fungal species *Stachybotrys chartarum*. Molecular and Cellular Probes 12, 387–396.

Desjardin, L.E., Chen, Y., Perkins, M.D., Teixeira, L., Cave, M.D. & Eisenach, K.D. (1998). Comparison of the ABI 7700 system (TaqMan) and competitive PCR for quantification of IS6110 DNA in sputum during treatment of tuberculosis. Journal of Clinical Microbiology 36, 1964–1968.

Haugland, R. A. et al.: "Quantitative Measurement of *Stachybotrys chartarum* conidia Using Real Time Detection of PCR Products with the TaqMan™ Fluorogenic Probe System," Molecular and Cellular Probes, Academic Press, London, GB, vol. 13, No. 5, Oct. 1999, pp. 329–340.

International Search Report, International Application No. PCT/US 02/06335, dated Jul. 10, 2003.

Roe, J. D. et al.: "Quantification of *Stachybotrys chartarum* conidia in Indoor Dust Using Real Time, Fluorescent Probe–Based Detection of PCR Products," Journal of Exposure Analysis and Environmental Epidemiology, Princeton Scientific Pub. Co., Princeton, N.J., U.S., vol. 11, No. 1, Jan. 2001, pp. 12–20.

Haugland & Heckman: "Identification of Putative Sequence Specific Primers for Detection of the Toxigenic Fungal Species *Stachybotrys chartarum*," Molecular and Cellular Probes, vol. 12, 1998, pp., 387–396.

Heid, C. A. et al.: "Real Time Quantitative PCR," Genome Research, Cold Spring Harbor Laboratory Press, U.S., vol. 6, No. 10, Oct. 1, 1996, pp. 986–994.

Cruz–Perez, P. et al.: "Specific Detection of *Stachybotrys chartarum* in Pure Culture Using Quantitative Polymerase Chain Reaction," Molecular and Cellular Probes, vol. 15, No. 3, Jun. 2001, pp. 129–138.

* cited by examiner

Primary Examiner—Kenneth R. Horlick
Assistant Examiner—Cynthia Wilder (57) ABSTRACT

A method for detecting the fungus *Stachybotrys chartarum* includes isolating DNA from a sample suspected of containing the fungus *Stachybotrys chartarum*. The method further includes subjecting the DNA to polymerase chain reaction amplification utilizing at least one of several primers, the several primers each including one of the base sequences 5'GTTGCTTCGGCGGGAAC3', 5'TTTGCGTTTGCCACTCAGAG3', 5'ACCTATCGTTGCTTCGGCG3', and 5'GCGTTTGC-CACTCAGAGAATACT3'. The method additionally includes detecting the fungus *Stachybotrys chartarum* by visualizing the product of the polymerase chain reaction.

17 Claims, 8 Drawing Sheets

```
START
  ↓
105 — OBTAIN AGAR PLATES CONTAINING PURE CULTURE OF Stachybotrys chartarum
  ↓
110 — FLOOD AGAR PLATES WITH BUFFER SOLUTION AND GENTLY AGITATE SURFACE OF COLONY WITH STERILE ROD TO CREATE SPORE SUSPENSION
  ↓
115 — COMBINE SPORE SUSPENSIONS FROM SEVERAL AGAR PLATES INTO A STERILE CENTRIFUGE TUBE AND THEN CENTRIFUGE
  ↓
120 — REMOVE THE SUPERNATANT FROM CENTRIFUGE TUBE WITHOUT DISTURBING THE PELLET
  ↓
125 — WASH AND CENTRIFUGE THE SPORE PELLET THREE TIMES WITH 10 ml PBT
  ↓
130 — RESUSPEND THE SPORE PELLET IN PBT AND STORE UNTIL READY TO USE
  ↓
135 — TO REMOVE SPORE AND/OR HYPHAL FRAGMENTS FROM SPORE SUSPENSION, PERFORM SUCROSE CENTRIFUGATION: ADD 1 ml OF SPORE SUSPENSION TO 25 ml OF FILTER-STERILIZED 0.35 M SUCROSE AND THEN CENTRIFUGE
  ↓
 (1) FIG. 2
```

FIG. 1

```
            ( 1 )  FIG. 1
               │
               ▼
205  ┌─────────────────────────────────────────────┐
     │ REMOVE SUPERNATANT FROM CENTRIFUGED SPORE   │
     │ SUSPENSION WITHOUT DISTURBING THE PELLET    │
     └─────────────────────────────────────────────┘
               │
               ▼
210  ┌─────────────────────────────────────────────┐
     │ RESUSPEND THE SPORE PELLET WITH RESIDUAL    │
     │ SUCROSE IN PBT AND STORE AT 4° C OVERNIGHT TO│
     │ SETTLE                                      │
     └─────────────────────────────────────────────┘
               │
               ▼
215  ┌─────────────────────────────────────────────┐
     │ REMOVE CLOUDY SUPERNATANTS ABOVE SPORE      │
     │ PELLETS AND RESUSPEND THE SPORE PELLET IN   │
     │ PBT                                         │
     └─────────────────────────────────────────────┘
               │
               ▼
220  ┌─────────────────────────────────────────────┐
     │ WHEN NECESSARY, PERFORM A SECOND SUCROSE    │
     │ CENTRIFUGATION USING 0.70 M SUCROSE         │
     └─────────────────────────────────────────────┘
               │
               ▼
225  ┌─────────────────────────────────────────────┐
     │ STORE S. chartarum SPORE SUSPENSIONS AT -70° C│
     │ UNTIL READY FOR USE                         │
     └─────────────────────────────────────────────┘
               │
               ▼
             ( END )
```

```
START
  ↓
405 — OBTAIN SAMPLE OF FUNGUS SUSPECTED OF BEING S. chartarum
  ↓
410 — SAMPLE FUNGAL SAMPLE WITH A STERILE COTTON SWAB
  ↓
415 — SUSPEND SWAB IN BUFFER SOLUTION
  ↓
420 — VORTEX BUFFER SOLUTION
  ↓
425 — ASEPTICALLY REMOVE SWAB FROM BUFFER SOLUTION
  ↓
430 — ALIQUOT 500 µL AND PLACE IN A MICROCENTRIFUGE TUBE
  ↓
 (2)   FIGS. 5 OR 6
```

METHOD FOR DETECTION OF STACHYBOTRYS CHARTARUM IN PURE CULTURE AND FIELD SAMPLES USING QUANTITATIVE POLYMERASE CHAIN REACTION

RELATED APPLICATION

This application claims priority under 35 U.S.C. §119 based on U.S. Provisional Application No. 60/280,712 filed Mar. 29, 2001, the disclosure of which is incorporated herein by reference.

GOVERNMENT CONTRACT

This invention was made with Government support under DE-FG03-98ER62574 awarded by the U.S. Department of Energy. The Government has certain rights in this invention.

FIELD OF THE INVENTION

The present invention relates generally to methods for detecting fungi and, more particularly, to methods for the detection and quantitation of the fungus *Stachybotrys chartarum* by means of genetic amplification of a specimen.

BACKGROUND OF THE INVENTION

Molds are ubiquitous in nature and are essential in nutrient cycling. The habitat or habitats that a mold occupies depend on several factors such as the kind and availability of nutrients, competition and spore dispersal. Fungi can occupy natural and man-made habitats in indoor and outdoor environments. These habitats include dead or living plants, decaying or freshly cut wood, food, grains, water and soil. Man-made products such as paint, wallpaper, and cellulose products (e.g., paper, cardboard, and wood derivatives) can be colonized and damaged by fungi, especially under humid or wet conditions. Certain molds can produce toxins that can cause health effects upon direct contact with skin, inhalation or ingestion.

Traditional methods of fungal identification include culture and microscopy analyses. However, these methods are laborious, time-consuming and require expertise. In addition, certain fungi are capable of causing health effects whether they are culturable or non-culturable. Other fungi are unable to produce classical structures under laboratory conditions that are necessary for identification. *Stachybotrys chartarum* is a toxigenic mold that has been implicated in the appearance of health effects in exposed individuals. This slow growing mold can colonize wet materials composed of cellulose. However, due to its specific nutrient and humidity requirements and the competition of other fungi, *S. chartarum* is often underestimated in traditional culture analyses.

Recently, analytical methods have been developed for rapidly and accurately detecting airborne bacteria (Alvarez, A. J., Buttner, M. P., Toranzos, G. A. et al. (1994). The use of solid-phase polymerase chain reaction for the enhanced detection of airborne microorganisms. Applied and Environmental Microbiology 60, 374–376; Alvarez, A. J., Buttner, M. P. & Stetzenbach, L. D. (1995). PCR for bioaerosol monitoring: sensitivity and environmental interference. Applied and Environmental Microbiology 61, 3639–3644), virus (Sawyer, M. H., Chamberlin, C. J., Wu, Y. N., Aintablian, N., & Wallace, M. R. (1994). Detection of varicella-zoster virus DNA in air samples from hospital rooms. Journal of Infectious Disease 169, 91–94) and fungi (Haugland, R. A., Vesper, S. J. & Wymer, L. J. (1999). Quantitative measurement of *Stachybotrys chartarum* conidia using real time detection of PCR products with the TaqMan™ fluorogenic probe system. Molecular and Cellular Probes 13, 329–340; Leenders, A.C.A.P., Van Belkum, A., Behrendt, M., Luijendijk, A. & Verbrugh, H. A. (1999). Density and molecular epidemiology of Aspergillus in air and relationship to outbreaks of Aspergillus infection. Journal of Clinical Microbiology 37, 1752–1757; Vesper, S., Dearborn, D. G., Yike, I. et al. (2000). Evaluation of *Stachybotrys chartarum* in the house of an infant with pulmonary hemorrhage: quantitative assessment before, during, and after remediation. Journal of Urban Health 77, 68–84). These methods use the polymerase chain reaction (PCR) to detect specific microorganisms by amplifying DNA sequences unique to the organism of interest. To use the PCR technique, sequence information must be first identified for a specific target DNA segment. Once an appropriate DNA sequence has been identified, oligonucleotide primers are selected, synthesized, and then tested for sensitivity, specificity, and selectivity. A fluorogenic nuclease assay in conjunction with a sequence detector (ABI PRISM 7700 Sequence Detection System, Applied Biosystems, Foster City, Calif.) has recently been developed as a means to amplify and quantitate PCR products, thus, eliminating the need for post-PCR gel electrophoresis for visualization of results (Heid, C. A., Stevens, J., Livak, K. J. & Williams, P. M. (1996). Real time quantitative PCR. Genome Research 6, 986–994). This method utilizes a fluorescently labeled oligonucleotide probe that anneals between the primers of choice as the amplification reaction proceeds, allowing for the determination of starting copy number of target DNA. The TaqMan™ assay that is integral to this quantitative technology has been previously validated by other researchers with DNA extracted from *Mycobacterium tuberculosis, Listeria monocytogenes* and Salmonella.

PCR detection of *S. chartarum* has been reported (Haugland, R. A. & Heckman, J. L. (1998). Identification of putative sequence specific PCR primers for detection of the toxigenic fungal species *Stachybotrys chartarum*. Molecular and Cellular Probes 12, 387–396; Haugland et al., 1999; Vesper et al., 2000), and quantitative PCR (QPCR) with the TaqMan™ assay has been used for the detection of *S. chartarum* in pure culture and air samples. However, quantitation of the target organism was estimated based on the co-amplification of another fungus (i.e., *Geotrichum candidum*) and not on direct comparison to *S. chartarum* standards (absolute quantitation). The method of estimated quantitation requires that the organisms co-amplifying have identical primer binding sites and amplification efficiencies, requiring the need for post-PCR processing in order to distinguish the products generated (Heid et al., 1996). In addition, estimated quantitation is inaccurate in cases where PCR inhibitors co-extract with the DNA (Desjardin, L. E., Chen, Y., Perkins, M. D., Teixeira, L., Cave, M. D. & Eisenach, K. D. (1998). Comparison of the ABI 7700 system (TaqMan) and competitive PCR for quantification of IS6110 DNA in sputum during treatment of tuberculosis. Journal of Clinical Microbiology 36, 1964–1968; Haugland et al., 1999).

Therefore, there exists a need for the development of QPCR methods for the detection and absolute quantitation of *S. chartarum*.

SUMMARY OF THE INVENTION

Methods consistent with the present invention address this need and others by employing QPCR with novel primers for detecting and quantitating *S. chartarum* without the necessity of further employing estimated quantitation techniques. Quantitation of samples suspected of containing *S. chartarum*, consistent with the present invention, may be based on direct comparison to *S. chartarum* standards (absolute quantitation), thus, avoiding the inaccuracies of estimated quantitation where PCR inhibitors may co-extract with the DNA. The primer and probe set used in QPCR consistent with the present invention may include oligonucleotide primers and a fluorescent probe that were designed from the internal transcribed spacer region (ITS 1) of the 18S rRNA gene of the species *S. chartarum*.

In accordance with the purpose of the invention as embodied and broadly described herein, a method for detecting the fungus *Stachybotrys chartarum* includes isolating DNA from a sample suspected of containing the fungus *Stachybotrys chartarum*; subjecting the DNA to polymerase chain reaction amplification utilizing at least one primer, wherein the at least one primer comprises one of (SEQ ID NO: 1) 5'GTTGCTTCGGCGGGAAC3'(SEQ ID NO: 2) 5'TTTGCGTTTGCCACTCAGAG3', (SEQ ID NO: 3) 5'ACCTATCGTTGCTTCGGCG3', and (SEQ ID NO: 4) 5'GCGTTTGCCACTCAGAGAATACT3'base sequence; and detecting the fungus *Stachybotrys chartarum* by visualizing the product of the polymerase chain reaction.

In another exemplary embodiment consistent with the invention, a primer set for detecting *Stachybotrys chartarum* using polymerase chain reaction includes a first primer comprising a base sequence (SEQ ID NO: 1) 5'GTTGCT-TCGGCGGGAAC3'; and a second primer comprising a base sequence (SEQ ID NO: 2) 5'TTTGCGTTTGCCACT-CAGAG3'.

In a further exemplary embodiment consistent with the invention, a primer set for detecting *Stachybotrys chartarum* using polymerase chain reaction includes a first primer comprising a first base sequence (SEQ ID NO: 3) 5'ACCTATCGTTGCTTCGGCG3'; and a second primer comprising a second base sequence (SEQ ID NO: 4) 5'GCGTTTGCCACTCAGAGAATACT3'.

In an additional exemplary embodiment consistent with the invention, a primer and probe set for detecting the fungus *Stachybotrys chartarum* using polymerase chain reaction includes a forward primer comprising base sequence (SEQ ID NO: 1) 5'GTTGCTTCGGCGGGAAC3'; a reverse primer comprising a base sequence (SEQ ID NO: 2) 5'TTTGCGTTTGCCACTCAGAG3'; and a probe comprising a base sequence (SEQ ID NO: 5) 6-FAM-5'CTGCGCCCGGATCCAGGC3'-TAMRA.

In another exemplary embodiment consistentwith the invention, a primer and probe set for detecting the fungus *Stachybotrys chartarum* using polymerase chain reaction, includes a forward primer comprising a first base sequence (SEQ ID NO: 3) 5'ACCTATCGTTGCTTCGGCG3'; a reverse primer comprising a second base sequence (SEQ ID NO: 4) 5'GCGTTTGCCACTCAGAGAATACT3'; and a probe comprising a base sequence (SEQ ID NO: 5) 6-FAM-5'CTGCGCCCGGATCCAGGC3'-TAMRA.

In a further exemplary embodiment consistent with the invention, a method for detecting the presence of the fungus *Stachybotrys chartarum* includes obtaining a sample from the environment; extracting DNA from the sample; and amplifying the extracted DNA by polymerase chain reaction utilizing one or more primers to obtain an indication of the presence of *Stachybotrys chartarum* in the sample, wherein the one or more primers comprise at least one of a (SEQ ID NO: 1) 5'GTTGCTTCGGCGGGAAC3, (SEQ ID NO: 2) 5'TTTGCGTTTGCCACTCAGAG3', (SEQ ID NO: 3) 5'ACCTATCGTTGCGGCG3', and (SEO ID NO: 4) 5'GCGTTTGCCACTCAGAGAATAcT3'base sequence.

In yet another cxemplary embodiment consistent with the present invention, a method for detecting the presence of the fungus *Stachybotrys chartarum* includes obtaining a sample from the environment; extracting DNA from the sample; and amplifying the extracted DNA by polymerase chain reaction utilizing a primer set to obtain an indication of the presence of *Stachybotrys chartarum* in the sample, wherein the primer set comprises: a forward primer comprising a first base sequence (SEQ ID NO: 3) 5'ACCTATCGTTGCTTCGGCG3', and a reverse primer comprising a second base sequence (SEQ ID NO: 4) 5'GCGTTTGCCACTCAGAGAATACT3'.

In a further exemplary embodiment consistent with the invention, a method for identifying and quantifying the presence of the fungus *Stachybotrys chartarum* in a collected sample includes obtaining a primer set and probe that is specific for the fungal species *Stachybotrys chartarum*; collecting the sample from the environment; extracting the sample's DNA; obtaining DNA standards from a culture of *Stachybotrys chartarum*; determining the concentration of *Stachybotrys chartarum* spores in the DNA standards; amplifying by polymerase chain reaction each of the DNA standards and the collected sample's DNA using the obtained primer set and probe; and comparing amplification plots obtained by polymerase chain reaction of each of the DNA standards and the collected sample's DNA to obtain an indication of the presence of the fungus *Stachybotrys chartarum* in the collected sample and a concentration of the fungus *Stachybotrys chartarum* in the collected sample.

BRIEF DESCRIPTION OF THE DRAWINGS

The accompanying drawings, which are incorporated in and constitute a part of this specification, illustrate embodiments of the invention and, together with the description, explain the invention. In the drawings.

DETAILED DESCRIPTION

The following detailed description of the invention refers to the accompanying drawings. The same reference numbers in different drawings identify the same or similar elements. Also, the following detailed description does not limit the invention. Instead, the scope of the invention is defined by the appended claims.

Systems and methods consistent with the present invention permit the absolute quantitation of *S. chartarum* in samples by performing QPCR with novel oligonucleotide primers. Through parallel amplifications of reference standards containing *S. chartarum* with unknown samples suspected of containing *S. chartarum*, an amplification plot of the references standards can be produced from which the concentration of the unknown samples may be interpolated.

Exemplary Quantitation

Standard Preparation Process

Figure 1:
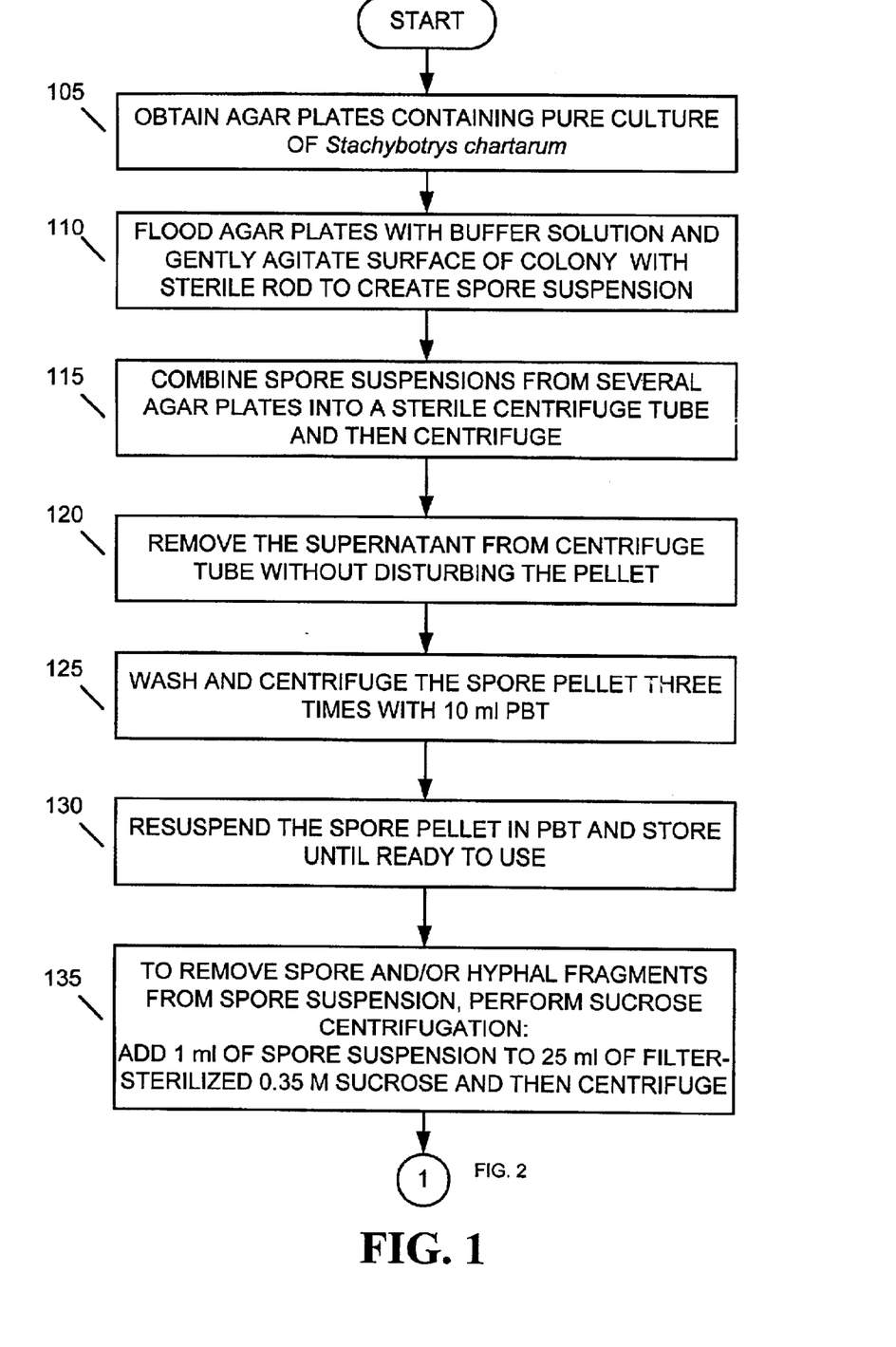
FIGS. 1–2 are flowcharts that illustrate an exemplary process, consistent with the present invention, for preparing *Stachybotrys chartarum* PCR quantitation standards.
Figure 2:
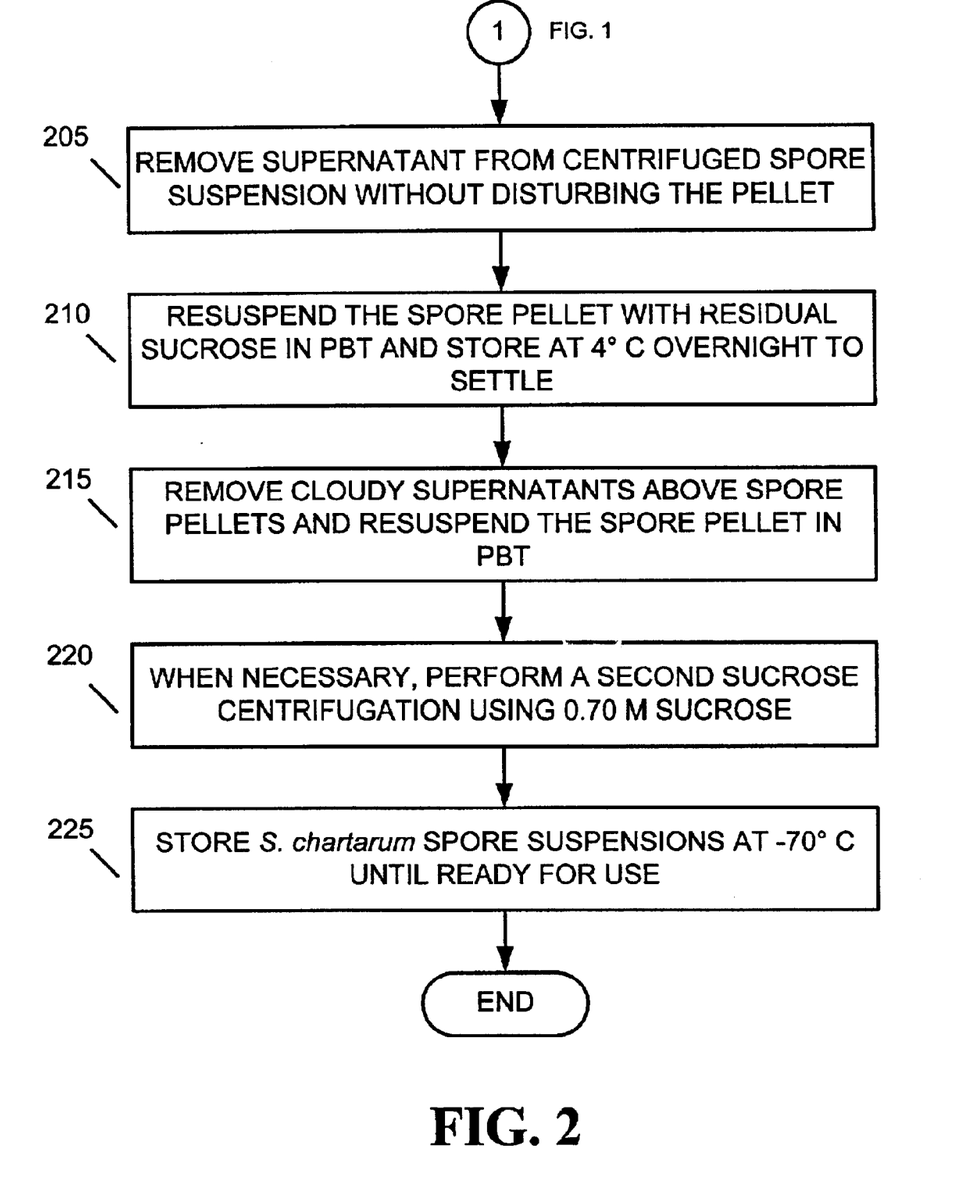
Figure 3:
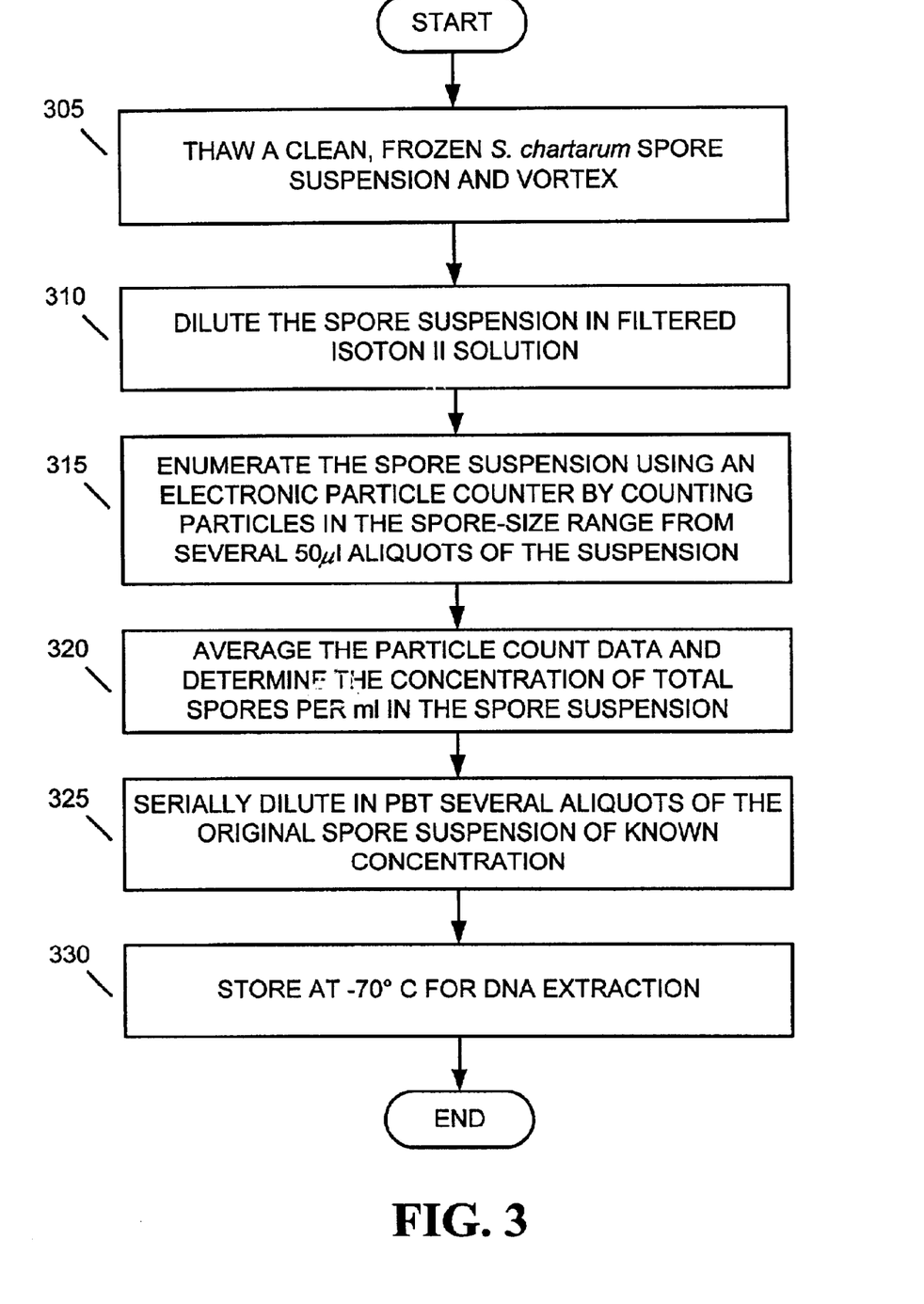
FIG. 3 is a flowchart that illustrates an exemplary process, consistent with the present invention, for enumerating quantitation standards for use in quantitative PCR.
Figure 4:
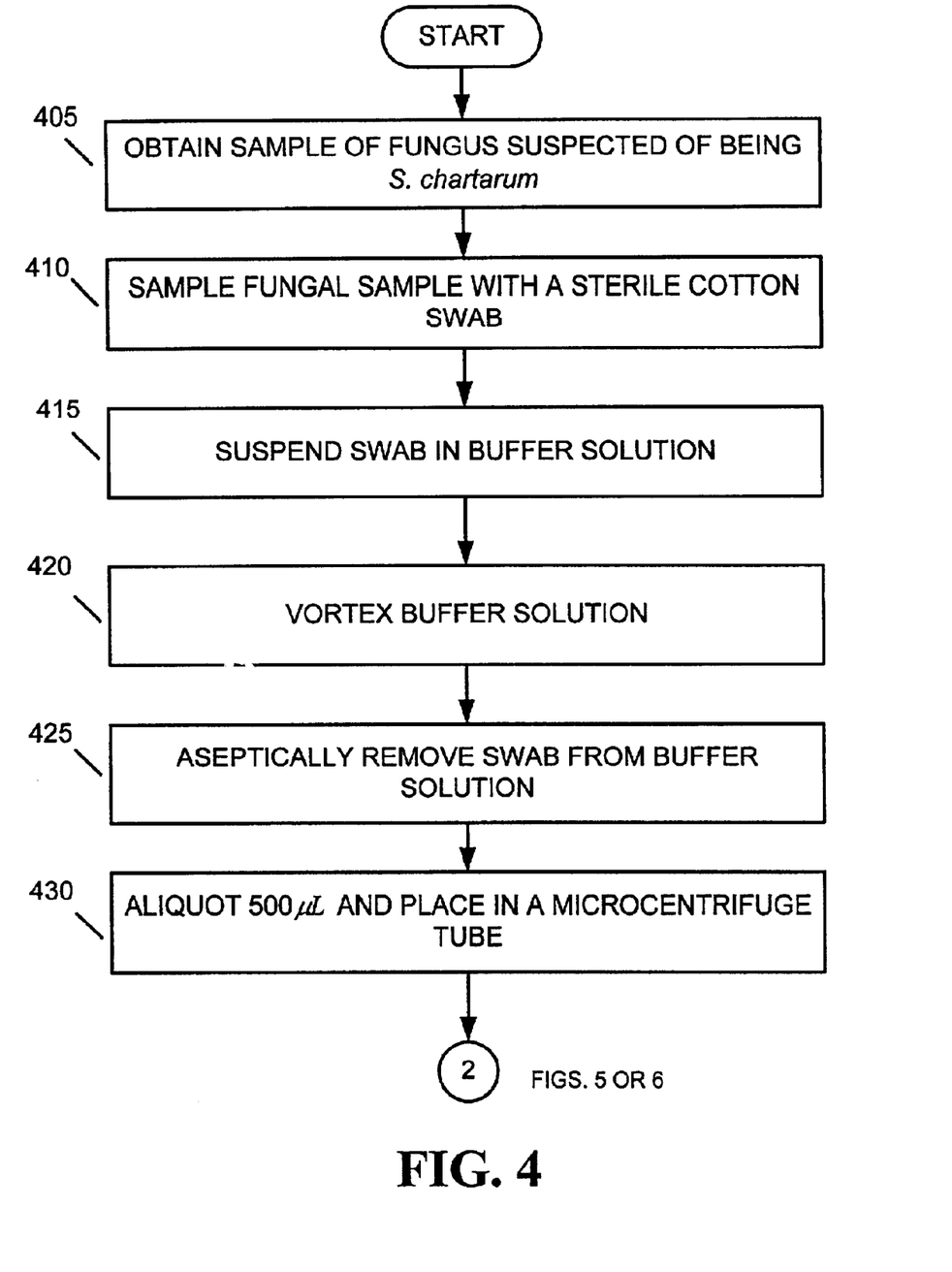
FIGS. 4–7 are flowcharts that illustrate an exemplary process, consistent with the present invention, for DNA amplification of a collected sample suspected of containing *Stachybotrys chartarum* using QPCR.

FIGS. 1–2 are flowcharts that illustrate an exemplary process, consistent with the present invention, for preparing S. chartarum PCR quantitation standards. The quantitation standards prepared in accordance with the exemplary process of FIGS. 1–2 may be enumerated (see FIG. 3 below) and then employed in QPCR for the absolute quantitation of S. chartarum in a sample (see FIGS. 4–8 below).

To begin the illustrated exemplary process, at least four agar plates containing pure cultures of Stachybotrys chartarum may first be obtained (step 105)(FIG. 1). The obtained agar plates may then be flooded with buffer solution and the surface of the S. chartarum colony may be gently agitated with a sterile rod to create a spore suspension in the buffer solution (step 110). The spore suspensions from several agar plates may be combined into a sterile centrifuge tube and the tube may then be centrifuged (step 115). For example, the spore suspensions may be placed in a 50 ml centrifuge tube and centrifuged at 11,500×g for 5 minutes at room temperature. After centrifuging the tube, the supernatant may be removed from the centrifuge tube without disturbing the remaining spore pellet (step 120). The remaining spore pellet may be washed and centrifuged three times with 10 ml PBT (step 125). The remaining spore pellet may be resuspended in 0.01 M potassium phosphate buffer with 0.05% Tween 20 (Sigma Chemical Co.)(PBT, pH 7.0) and stored until ready to use (step 130).

To remove spore and/or hyphal fragments from the spore suspension, sucrose centrifugation may be used. Sucrose centrifugation includes adding 1 ml of the spore suspension to approximately 25 ml of filter-sterilized 0.35M sucrose and centrifuging the resulting spore suspension at, for example, 1000×g for 10 minutes at room temperature (step 135). Following sucrose centrifugation, the supernatant may again be removed from the centrifuged spore suspension without disturbing the pellet (step 205)(FIG. 2). The spore pellet from the spore suspension may be resuspended with residual sucrose in, for example, 200 µL PBT and stored at 4° C. overnight to settle (step 210). Subsequent to overnight storage, cloudy supernatants above the spore pellet in the spore suspension may be removed and the spore pellet may be resuspended in PBT (step 215). When necessary, a second sucrose centrifugation may be performed using 0.70 M sucrose (step 220). The resulting S. chartarum spore suspensions may be stored at −70° C. until needed for use as quantitation standards in quantitative PCR (step 225).

Exemplary Quantitation

Standard Enumeration Process

FIG. 3 is a flowchart that illustrates an exemplary process, consistent with the present invention, for enumerating quantitation standards for use in quantitative PCR. Enumeration of the quantitation standards prepared, for example, according to the exemplary process described with respect to FIGS. 1–2 above, enables the construction of an amplification plot subsequent to QPCR DNA amplification (see FIGS. 4–8 below). Concentrations of *S. chartarum* in an amplified unknown sample may then be interpolated from the constructed amplification plot.

To begin the illustrated exemplary enumeration process, a clean, frozen *Stachybotrys chartarum* spore suspension, prepared in accordance with the exemplary process of FIGS. 1–2, may be thawed and then vortexed (step 305)(FIG. 3). The spore suspension may, for example, be vortexed at maximum speed for 1 minute. The spore suspension may be diluted in filtered Isoton II solution (Beckman Coulter, Inc.) (step 310). The spore suspension may then be enumerated using an electronic particle counter, such as, for example, a Coulter Multisizer II electronic particle counter, by counting particles in the spore-size range from several 50 μl aliquots (e.g., five) of the spore suspension (step 315). The particle count may be corrected, for example, using conventional coincidence correction techniques. The Coulter Multisizer II, for example, automatically performs coincidence correction of the particle count. The particle count data obtained using the electronic particle counter may be averaged and the concentration of total spores per ml in the spore suspension may be determined (step 320).

Several aliquots of the original spore suspension of known concentration ($10^0$ to $10^5$ spores/PCR reaction) may be serially diluted in PBT (step 325). Each of the several aliquots may be diluted such that they are exponentially separated. For example, each of the dilutions may be diluted using sequential dilution exponents (e.g., 1,2,3 4, etc.). The serially diluted aliquots of the spore suspension may then be stored at −70° C. for subsequent DNA extraction (step 330).

Exemplary Quantitative

Polymerase Chain Reaction Process

FIGS. 4–7 are flowcharts that illustrate an exemplary process for DNA extraction, purification and amplification of *S. chartarum* in a sample using QPCR, consistent with the present invention. By employing novel oligonucleotide primers and a fluorescent probe, the exemplary process of FIGS. 4–7 further enables the detection and absolute quantitation of *S. chartarum* in a sample through parallel amplifications of the reference quantitation standards, prepared in accordance with the exemplary process of FIGS. 1–3, with an unknown sample suspected of containing *S. chartarum.*

The exemplary process may begin by obtaining a sample of fungus suspected of being *S. chartarum* (step 405)(FIG. 4). The sample may include, for example, a pure culture of a fungus or a field sample. A suitable growth medium such as malt extract agar (MEA, pH 4.7, Difco Laboratories, Detroit, Mich.), potato dextrose agar (PDA, pH 5.6, Difco) or cellulose agar (CA, pH 8.0, formulation courtesy of W. Sorenson, NIOSH, Morgantown, W. Va. and B. Jarvis, University of Maryland, Md.) may be used. The agar-filled plates are inoculated with the fungal sample and incubated at 23° C. for 3–7 days. The cellulose agar may be formulated as follows:

1. For 1000 ml of distilled $H_2O$ add:
   - 2 g $NaNO_3$
   - 1 g $K_2HPO_4$
   - 0.5 g $MgSO_4$
   - 0.5 g KCl
   - 20 g cellulose powder (Sigmacell type; Sigma Chemical Co., St. Louis, Mo.)
   - 15 g granulated agar
   - 50 mg rose bengal
2. Adjust pH to 8.0
3. Sterilize
4. Pour into Petri dishes; protect from light The obtained fungal sample may be sampled by gently swabbing the surface of the fungal colony with a sterile cotton swab (step 410). The swab may then be suspended in 3 ml of a buffer solution (step 415). The buffer solution may include, for example, 0.01 M potassium phosphate buffer with 0.05% Tween 20 (Sigma Chemical Co.)(PBT, pH 7.0). The buffer solution, with suspended swab, may be vortexed on maximum speed for one minute, for example, using a conventional vortex mixer (step 420). The suspended swab may be aseptically removed from the buffer solution (step 425). 500 μl of the buffer solution containing the spore suspension may then be aliquotted and placed in, for example, a 2 ml microcentrifuge tube for DNA extraction (step 430).

Figure 5:
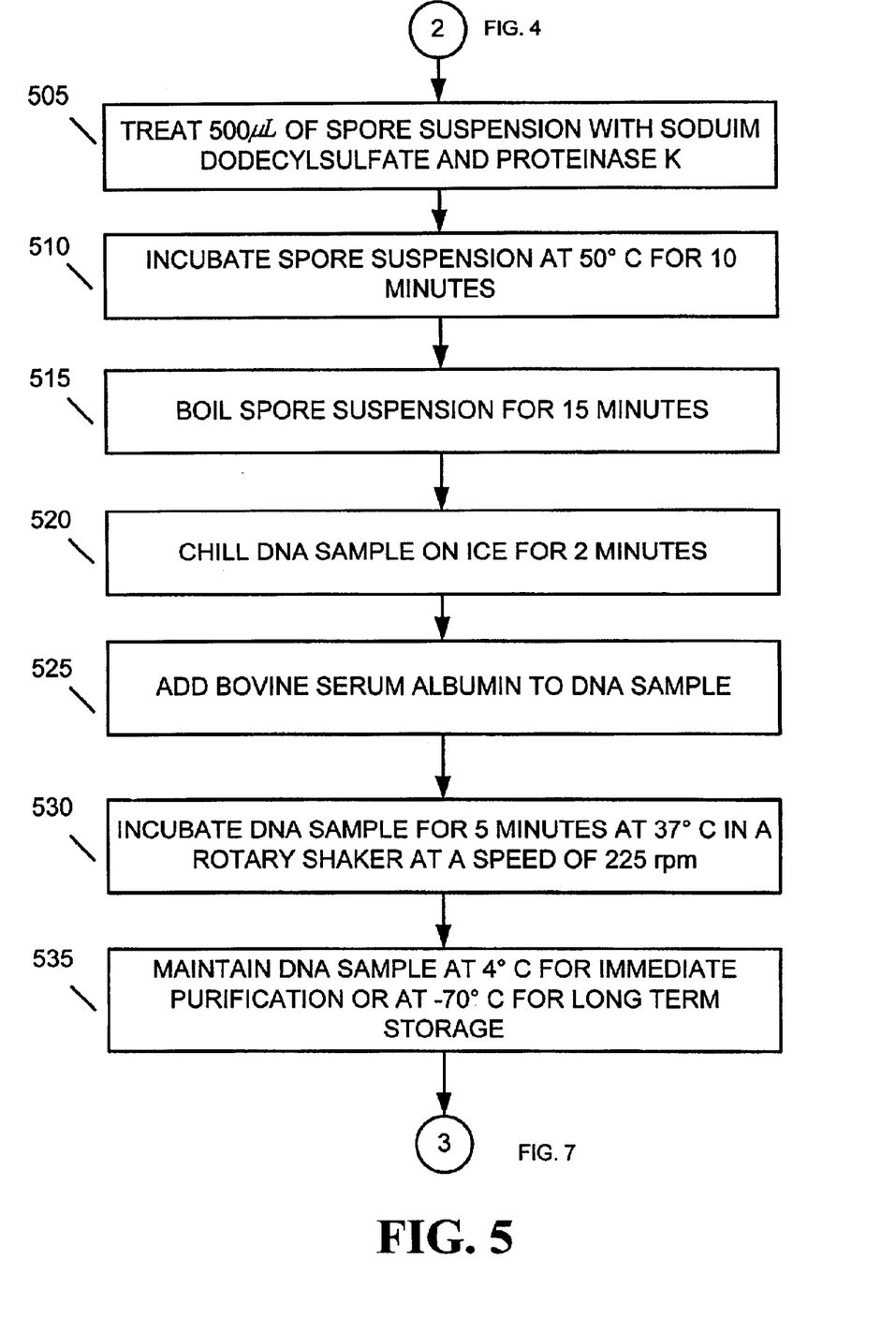

A number of techniques may be used for extracting the DNA from the spore suspension, including a boiling technique and a mechanic disruption technique. FIG. 5 details an exemplary boiling technique that includes treating the 500 μl contained in the microcentrifuge tube with sodium dodecyl-sulfate (0.5% final concentration) and proteinase K (20 μg/ml final concentration) (step 505). The treated spore suspension may then be incubated at, for example, 50° C. for 10 minutes (step 510). Subsequent to incubation, the spore suspension may be boiled for 15 minutes (step 515). The boiled sample may then be chilled on ice for, for example, 2 minutes (step 520). Bovine serum albumin may further be added to the chilled DNA sample (step 525). The DNA sample, with bovine serum albumin added, may be incubated for 5 minutes at 37° C. in a rotary shaker at, for example, a speed of 225 rpm (step 530). The DNA sample may be maintained at 4° C. for immediate purification, or at −70° C. for long term storage (step 535).

Figure 6:
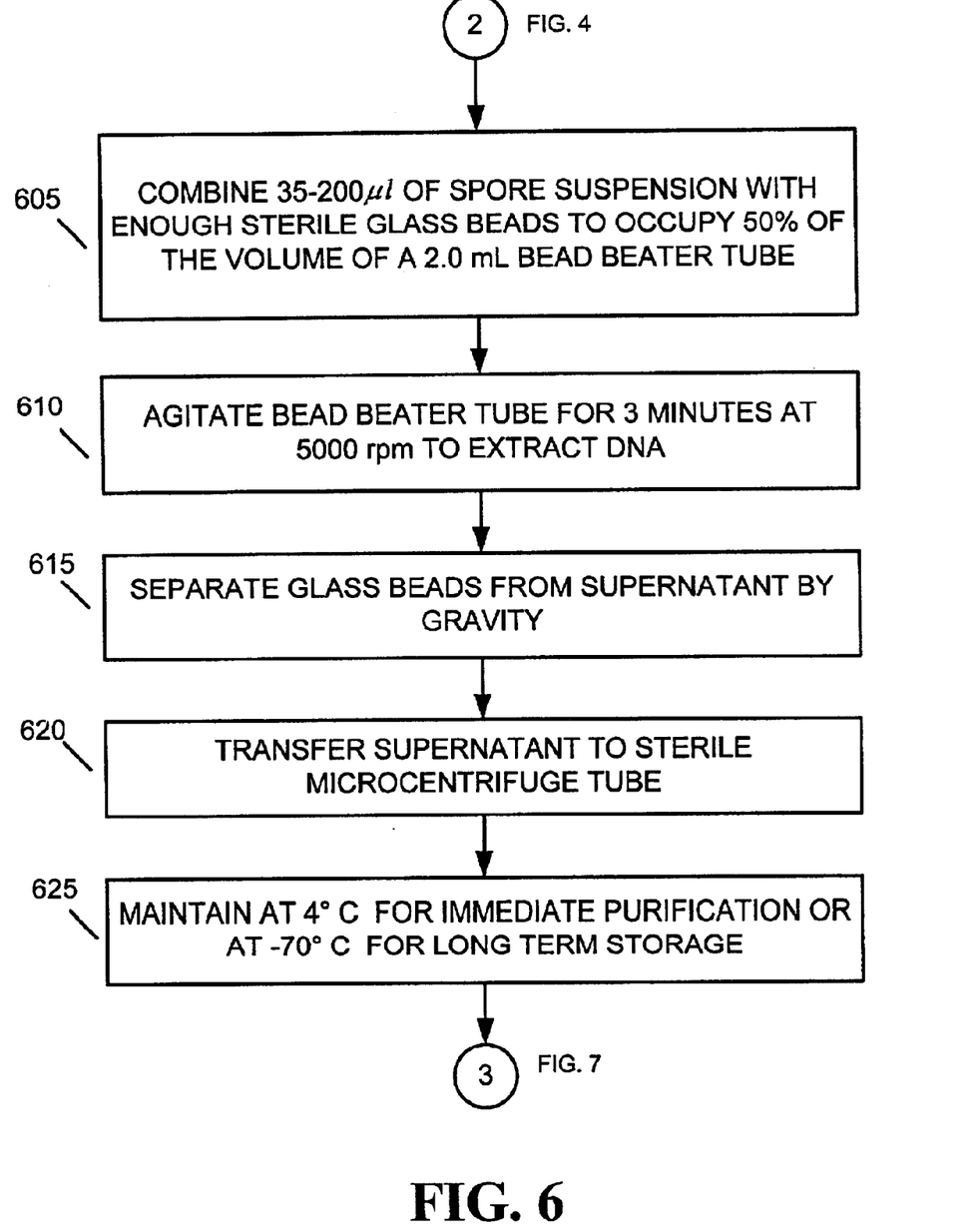

FIG. 6 details an exemplary bead beating technique for extracting the DNA from the spore suspension. This exemplary technique includes combining 35–200 μl of spore suspension with enough sterile glass beads to occupy 50% of the volume of a 2.0 ml bead beater tube (step 605). The bead beater tube may then be agitated for 3 minutes at 5000 rpm to extract the DNA. The glass beads may be separated from the supernatant by gravity (step 615). The separated supernatant may be transferred to a sterile microcentrifuge tube (step 620) and maintained at 4° C. for immediate purification, or at −70° C. for long term storage (step 625).

Subsequent to extraction of the DNA from the spore suspension, the DNA may be concentrated and purified (step 705)(FIG. 7) using any conventional DNA purification kit in accordance with the manufacturer's instructions. Such kits may include the Pellet Paint™ Co-precipitant kit, (Novagen, Madison, Wis., USA), the QIAamp Blood and Tissue kit (QIAGEN, Inc., Valencia, Calif., USA), the DNeasy Plant kit (Qiagen, Inc., Valencia, Calif.), the Master Pure Plant Leaf DNA Purification kit (Epicentre Technologies, Madison, Wis., USA), the EluQuik DNA Purification kit (Schleicher & Schuell, Keene, N.H., USA), the Dynabeads DNA DIRECT System I (Dynal, Inc., Lake Success, N.Y., USA), and the QIAGEN Genomic tip 20/G in conjunction with the Genomic DNA Buffer set (QIAGEN, Inc.).

Figure 7:
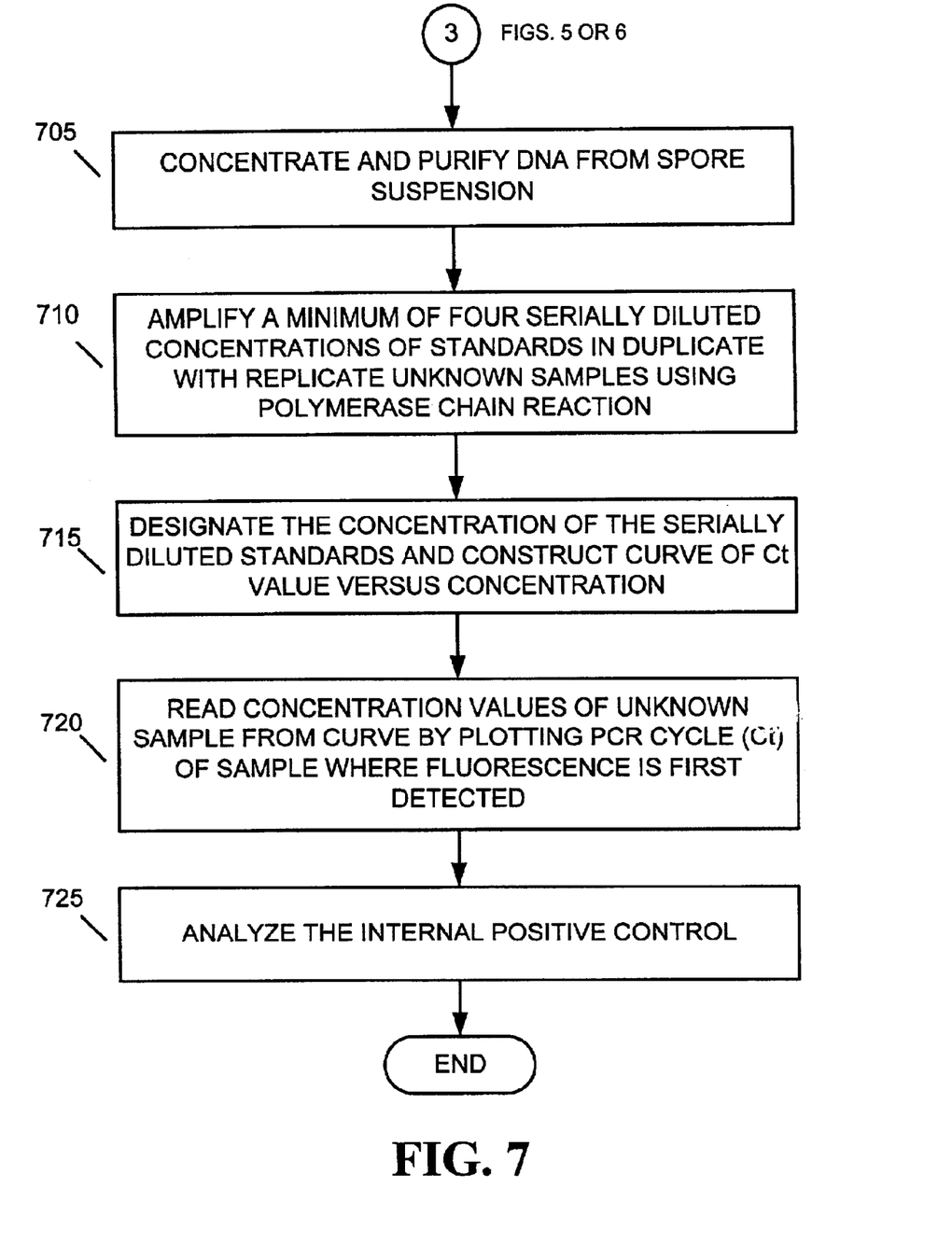

After concentration and purification of the spore suspension DNA, a minimum of four serially diluted concentrations of standards, in duplicate with replicate unknown samples, may be amplified by polymerase chain reaction. The ABI Prism 7700 Sequence Detection System (7700 SDS; Applied Biosystems, Foster City, Calif.) may be used, for example (step 710). Amplification conditions using, for example, Applied Biosystems reagents may include the following:

fungal DNA template (5 μl)

1 X TaqMan™ buffer A 5 mM MgCl$_2$ 0.1 mM dATP 0.1 mM dCTP 0.1 mM dGTP 0.2 mM dUTP 2.5 Ampli Taq Gold 0.5 AmpErase Uracyl N-Glycosylase 0.9 μM of each of the forward and reverse *S. chartarum* primers from either selected primer set:

Primer set 1:

forward (STAF1) primer: (SEQ ID NO:1) 5'GTTGCTTCGGCGGGAAC3' reverse (STAR1) primer: (SEQ ID NO:2) 5'TTTGCGTTTGCCACTCAGAG3'

Primer set 2:

forward (STAF2) primer: (SEQ ID NO:3) 5'ACCTATCGTTGCTTCGGCG3' reverse (STAR2) primer: (SEQ ID NO:4) 5'GCGTTTGCCACTCAGAGAATACT3'

0.2 μM of the following *S. chartarum* probe:
(SEQ ID NO: 5) 6-FAM-5'CTGCGCCCGGATCCAGGC3'-TAMRA 1X Exogenous Internal Positive Control mix (IPC with VIC™-labeled probe, Applied Biosystems)

1IPC DNA for a total reaction volume of 50 μl. TaqMan™ cycling conditions may include the following: 2 minutes at 50° C.; 10 minutes at 95° C.; 40 cycles of 15 seconds at 95° C. followed by 1 minute at 60° C.

Figure 8:
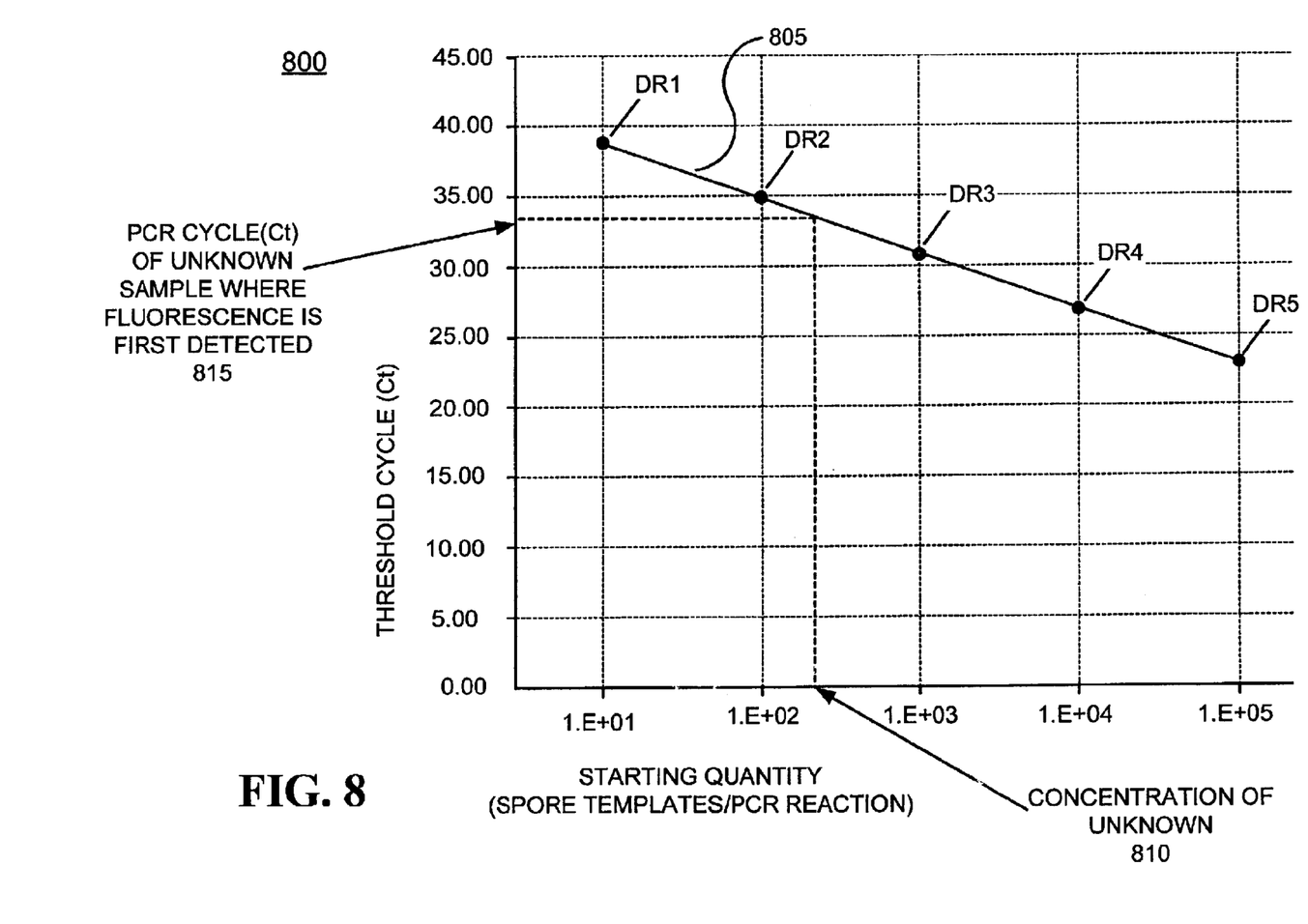
FIG. 8 is a plot of PCR cycle value (Ct) versus concentration for several *S. chartarum* quantitation standards.

After amplification, the concentration of the serially diluted *S. chartarum* standards may be designated and a curve of Ct value versus concentration may be constructed (step 715). The concentration of the serially diluted standards can be designated according to the concentration values determined at steps 320 and 325 above. Ct refers to the PCR cycle number where detectable amplification product is measured. The Ct value is inversely proportional to initial DNA template concentration. An exemplary curve 800 of Ct vs. concentration is illustrated in FIG. 8. Curve 800 depicts plots of the concentrations of each of the *S. chartarum* standards (DR1, DR2, DR3, DR4 and DR5) (x-axis) and the Ct value (y-axis), corresponding to each *S. chartarum* standard, at which fluorescence is first detected. Concentration values 810 of unknown samples may be interpolated from curve 800 by plotting the PCR cycle (Ct) 815 of the unknown sample where fluorescence is first detected (step 720). The internal positive control may further be analyzed, for example, according to the manufacturer's instructions (step 725). For example, the TaqMan® Exogenous Internal Positive Control Kit (IPC-Vic, Applied Biosystems, Foster City, Calif.) contains pre-optimized reagents that, when added to DNA samples for PCR amplification, can distinguish true negatives from false negative results due to inhibition. This kit contains control DNA, primers to amplify this control DNA, and a probe (labeled with the fluorescent dye Vic) that is specific for the control DNA. By adding all IPC kit reagents into the target sample ready for amplification, both the IPC and target DNA should amplify if no inhibitors are present. However, when inhibitors are present the IPC DNA is affected in the same way as the target DNA is affected, showing decreased or negative amplification results and therefore demonstrating the presence of inhibitors in the reaction.

EXAMPLES

Test Organisms and Culture Media

The fungus *S. chartarum* served as the test organism for this study. Forty fungi of interest representing 16 genera were obtained from the American Type Culture Collection (ATCC, Manassas, Va., USA) or from laboratory stocks and cultured in the laboratory (Table 1) (P&K isolates courtesy of C. Yang, P&K Microbiology Services, Cherry Hill, N.J., USA). Cellulose agar (CA, pH 8.0, formulation courtesy of W. Sorenson, NIOSH, Morgantown, W. Va., and B. Jarvis, University of Maryland, Md., USA) was used for the culture of Stachybotrys species. Malt extract agar (MEA, (pH 4.7), Difco Laboratories, Detroit, Mich., USA) and potato dextrose agar (PDA, (pH 5.6), Difco) were used for the culture of all other fungal species. All fungal cultures were incubated at 23° C. for 3–7 days.

TABLE 1

Fungal species tested

| Organism | Source |
| --- | --- |
| *Acremonium strictum* | ATCC 10141 |
| *Alternaria alternata* | ATCC 6663 |
| *Aspergillus niger* | ATCC 10535 |
| *Aspergillus versicolor* | HRC/UNLV |
| *Beauveria* sp. | HRC/UNLV |
| *Bipolaris* sp. | HRC/UNLV |
| *Chaetomium* sp. | HRC/UNLV |
| *Cladosporium herbarum* | ATCC 28987 |
| *Fusarium oxysporum* | ATCC 48112 |
| *Memnoniella echinata* | ATCC 32888 |
| *Memnoniella subsimplex* | ATCC 22700 |
| *Penicillium chrysogenum* | ATCC 9480 |
| *Penicillium expansum* | ATCC 7861 |
| *Phoma* sp. | HRC/UNLV |
| *Rhizopus* sp. | HRC/UNLV |
| *Stachybotrys chartarum* | ATCC 9182 |
| *Stachybotrys chartarum* | ATCC 201210 |
| *Stachybotrys chartarum* (10 isolates) | P&K |
| *Stachybotrys dichroa* | ATCC 18917 |
| *Stachybotrys microspora* | ATCC 18852 |
| *Stachybotrys nephrospora* | ATCC 22706 |
| *Stachybotrys* sp. (seven isolates) | HRC/UNLV |
| *Trichoderma* sp. | HRC/UNLV |
| *Ustilago* sp. | HRC/UNLV |
| *Verticillium* sp. | HRC/UNLV |

ATCC, American Type Culture Collection;
HRC/UNLV, Harry Reid Center for Environmental Studies, University of Nevada-Las Vegas;
P&K Microbiology Services, Cherry Hill, NJ.

Spore Harvest

Spores were harvested from two pure cultures of *S. chartarum* (ATCC 9182 and HRC/UNLV 1) to prepare standards of known concentration. Liquid spore harvests were performed for *S. chartarum* using the method of Crow et al., with modifications. In brief, this method consisted of flooding the plates with 3 ml of 0.01 M phosphate buffer with 0.05% (v/v) Tween 20 (Sigma Chemical Company, St. Louis, Mo., USA) (PBT (pH 7.0)) and gently agitating the surface of the colony with a sterile L-shaped glass rod. The spore suspensions from at least four plates were combined into a sterile 50 ml centrifuge tube and centrifuged at 11,500×g for 5 min. at room temperature. The supernatant was removed without disturbing the spore pellet and the spores were washed and centrifuged three times with 10 ml PBT. The final spore pellet was suspended in 1 ml PBT and stored at −70° C. until ready for use.

Two methods were tested for the removal of spore and/or hyphal fragments from spore suspensions. One cleaning method consisted of filtration of the *S. chartarum* spore suspension through 2 or 3 $\mu$m membranes (Millipore Corp., Bedford, Mass., USA). Membranes tested were: mixed cellulose ester, 3 $\mu$m; polycarbonate, 2 and 3 $\mu$m; and teflon, 3 $\mu$m. Sucrose density centrifugation was also tested for the removal of spore fragments.

One ml of spore suspension was added to approximately 25 ml of filter-sterilized sucrose (0.35 M) and centrifuged at 1000×g for 10 mm. at room temperature (Wang, NS) The supernatant was removed without disturbing the pellet. The spore pellet with residual sucrose was resuspended in 200 $\mu$l PBT and stored at 40° C. overnight to settle. Cloudy supernatants above spore pellets were removed and the spore pellet was resuspended in PBT as before. Effectiveness of the cleaning methods was assessed by enumeration of the spore suspensions with an electronic particle counter (see PCR quantitation standards and analysis section). When necessary, a second sucrose centrifugation was performed using 0.70 M sucrose. Clean spore suspensions were stored at −70° C. until ready for use.

Primer Design and PCR Amplification

*Stachybotrys chartarum* sequences for the 18 S rRna gene were obtained from GenBank and compared against all other sequences available on-line with the Basic Local Alignment Search Tool algorithm (BLAST, National Center for Biotechnology Information, National Institutes of Health). Two sets of primers and probes were designed using the Primer Express software (Applied Biosystems) and obtained from commercial sources (Operon Technologies, Alameda, Calif., USA; Synthetic Genetics, San Diego, Calif., USA).

The ABI Prism 7700 Sequence Detection System (7700 SDS; Applied Biosystems) was used for PCR analysis. Amplification conditions using the Applied Biosystems reagents were as follows: fungal DNA template (5 $\mu$l); 1×TaqMan™ buffer A; 5 mM MgCl$_2$; 0.1 mM dATP; 0.1 mM dCTP; 0.1 mM dGTP; 0.2 mM dUTP; 2.5 U Ampli Taq Gold; 0.5 U AmpErase Uracyl N-Glycosylase; 0.2–0.9 $\mu$M each primer (Operon Technologies, Alameda, Calif., USA); 0.2 $\mu$M probe (Synthetic Genetics, San Diego, Calif., USA), for a total reaction volume of 50 $\mu$l. An internal positive control (IPC Vic Probe, Applied Biosystems) was incorporated into the PCR reaction to determine whether samples contained PCR inhibitors. The IPC was obtained with a fluorescent probe containing a dye different from that of the target DNA probe to allow for the differentiation of fluorescent signals generated during amplification. TaqMan™ cycling-conditions were as follows: 2 min. at 50° C.; 10 min. at 95° C.; 40 cycles of 15 s at 95° C. followed by 1 min. a *Stachybotrys chartarum* DNA obtained from the ATCC strain 9182 was used for testing the *S. chartarum* primers. Primer optimization consisted of testing combinations from 50 nM to 900 nM for the forward and reverse primers with control DNA from the target organism.

DNA Extraction and Purification

Two methods were tested for the DNA extraction from *S. chartarum* spores: a boiling protocol developed for DNA extraction of bacterial endospores and mechanic disruption using a Mini Bead Beater (Biospec Products, Inc., Bartlesville, Okla., USA). The boiling protocol consisted of treating 10 to 500 μl of the spore suspension with sodium dodecylsulfate 0.5% (v/v) final concentration and proteinase K (20 μg/ml final concentration), followed by incubation at 50° C. for 10 min. and boiling for 15 min. The samples were chilled on ice for 2 min. and bovine serum albumin was added to a final concentration of 0.05% (w/v). The samples were incubated for 5 min. at 37° C. in a rotary shaker at a speed of 225 rpm. The DNA was maintained at 4° C. for immediate purification or at −70° C. for long-term storage. The bead beating protocol consisted of combining 35–200 μl of *S. chartarum* spore suspension with enough sterile glass beads (0.1 mm) to make 50% of the volume occupied by the sample and the beads in a 2.0 ml bead beater tube. The sample was agitated for 3 min. at 5000 rpm. Separation of the glass beads from the supernatant occurred by gravity. The supernatant was transferred to a sterile microcentrifuge tube and maintained at 4° C. for immediate purification or at −70° C. for long-term storage.

A series of commercially available kits were tested for the concentration and purification of DNA. The kits tested following the manufacturer's protocols were: Pellet Paint Co-precipitant (Novagen, Madison, Wis., USA), QIAamp Blood and Tissue kit (QIAGEN, Inc. Valencia, Calif., USA), DNeasy Plant kit (QIAGEN, Inc.), Master Pure Plant Leaf DNA Purification kit (Epicentre Technologies, Madison, Wis., USA), EluQuik DNA Purification kit (Schleicher & Schuell, Keene, N.H., USA), Dynabeads DNA DIRECT System I (Dynal, Inc., Lake Success, N.Y., USA), and QIAGEN Genomic tip 20/G in conjunction with the Genomic DNA buffer set (QIAGEN, Inc.)

The effect of sample volume on the efficiency of the extraction/purification protocols in removing PCR inhibitors was determined. Ten, 100 and 500 μl spore suspension volumes of two *S. chartarum* laboratory isolates (HRC/UNLV 6 and P&K 0177) were extracted by one of two methods: (i) boiling/Pellet Paint/DNeasy Plant kit; or (ii) boiling/Pellet Paint/Elu-Quick DNA Purification kit.

Specificity Testing

For PCR primer specificity testing, pure cultures were sampled by gently swabbing the surface of the fungal colony with a cotton swab and resuspending in 3 ml PBT. After vortexing on maximum speed for 1 min., the swab was removed. Aliquots of 500 μl were placed in 2 ml microcentrifuge tubes for subsequent DNA extraction. Samples and aliquots were stored at −70° C. Extraction was performed using the boiling method as described above followed by Pellet Paint purification. The purified DNA was subjected to PCR amplification using the designed primers and probe for *S. chartarum*.

An ethidium bromide dot quantitation method was utilized for the determination of the presence of DNA on samples prepared for specificity testing. DNA controls were prepared by serial dilutions of a 100 bp DNA ladder (Promega, Madison, Wis., USA) in TrisEDTA buffer (TE (pH 8.0)) to obtain concentrations of 1.3, 13.0 and 130.0 μg/ml. Four microlitres of control or sample DNA was combined with an equal volume of ethidium bromide (1 μg/ml, final concentration) and mixed by vortexing. Negative controls were prepared by substituting TE buffer for DNA. Mixed samples were applied in the form of a dot onto a piece of plastic wrap stretched over the surface of an U.V. transilluminator. A permanent record of the dots was obtained by photographing with a Polaroid MP 4+ Instant Camera System (Fotodyne Inc., Hartland, Wis., USA).

PCR Quantitation Standards and Analysis

Total concentrations of cleaned *S. chartarum* spore suspensions (ATCC 9182 and HRC/UNLV 1) were determined using a Coulter Multisizer II electronic particle counter (Beckman Coulter, Inc., Miami, Fla., USA). A frozen liquid spore suspension of *S. chartarum* was thawed and vortexed for 1 min. The spore suspension was then diluted in filtered Isoton II solution (Beckman Coulter, Inc.) and enumerated using a Coulter Multisizer II. Five 50-μl aliquots of the sample were counted. The data were automatically adjusted for coincidence correction by the instrument and the particles in the spore-size range were counted (2.5 to 7.0 μm for the ATCC strain, 3.5 to 9.0 for the HRC/UNLV strain). The data were averaged and the concentration of total spores per ml in the spore suspensions were determined. Aliquots of the *S. chartarum* spore suspensions (ATCC 9182 and HRC/UNLV 1) of known concentration were serially diluted in PBT and stored at −70° C. for DNA extraction.

Quantitation using the 7700 SDS was accomplished by the use of standards of known concentration, processed in the same manner as the unknown samples. Standards ($10^0$ to $10^5$ template/reaction) were amplified in duplicate with replicate unknown samples. After amplification, the data were analyzed using the software provided with the 7700 SDS. The concentration of the standards was designated and the software constructed a standard curve of Ct value vs. concentration. Ct refers to the PCR cycle number where detectable amplification product is measured and the Ct value is inversely proportional to initial DNA template concentration. Concentration values for the unknown samples were extrapolated from the standard curve by the software and reported as the mean of two replicates. The internal positive control was analyzed according to the manufacturer's instructions. ATCC and laboratory *S. chartarum* isolates were enumerated with the Coulter Multisizer II and quantitated with the 7700 SDS to test the efficiency of the quantitation standards prepared.

Results

Primer Selection and Specificity

Primer design using the Primer Express software generated a list of primers and probes for the internal transcribed spacer (ITS1) of the 18S rRNA sequence of *S. chartarum* (GenBank accession # AF081468). Two primer sets designed around the same fluorescent probe were selected.

One primer set had the sequences (SEQ. ID NO. 1) 5'GTTGCTTCGGCGGGAAC3' and (SEQ. ID NO. 2) 5'TTTGCGTTTGCCACTCAGAG3' for the forward (STAF1) and reverse (STAR1) primers, respectively. This primer set produced a 107-bp amplicon. The additional primer set had the sequences (SEQ. ID NO. 3) 5'ACCTATCGTTGCTTCGGCG3' and (SEQ. ID NO. 4) 5'GCGTTTGCCACTCAGAGAATACT3' for the forward (STAF2) and reverse (STAR2) primers, respectively. This primer set produced a 111 bp amplicon. The fluorescent probe used for both primer sets had the sequence (SEQ. ID NO. 5) 6-FAM-5'CTGCGCCCGGATCCAGGC3'-TAMRA.

Both primer sets designed for *S. chartarum* amplified control DNA from *S. chartarum* ATCC strain 9182. PCR optimization of the two primer sets showed that combinations containing 900 nM forward and reverse primer were optimal (data not shown). Sensitivity of detection was tested with dilutions of control DNA in order to select one primer set for *S. chartarum*. The STAF1 and STAR1 primers were slightly more sensitive than the STAF2/STAR2 primer set (data not shown). Therefore, the STAF1/STAR1 primer set was selected for further tests.

*Stachybotrys chartarum* primers amplified two ATCC and 17 *S. chartarum* laboratory isolates (Table 2). They did not amplify fungal DNA extracted from 21 other fungal species (comprising 16 fungal genera), including three non-chartarum Stachybotrys species and two Memnoniella species. Three of seven Stachybotrys sp. isolates from the Las Vegas area and 10 *S. chartarum* isolates initially showed negative amplification with the *S. chartarum* primer set. However, dilution of these negative DNA samples produced positive PCR results.

TABLE 2

PCR results obtained for the specificity testing of *Stachybotrys chartarum* primers STAF1 and STAR1.

| Organism | PCR results |
|---|---|
| *Stachybotrys chartarum* (ATCC 9182) | + |
| *S. chartarum* (ATCC 201210) | + |
| *S. chartarum* (P&K 0060) | +* |
| *S. chartarum* (P&K 0061) | +* |
| *S. chartarum* (P&K 0062) | +* |
| *S. chartarum* (P&K 0063) | +* |
| *S. chartarum* (P&K 0045) | +* |
| *S. chartarum* (P&K 0175) | +* |
| *S. chartarum* (P&K 0177) | +* |
| *S. chartarum* (P&K 0179) | +* |
| *S. chartarum* (P&K 0180) | +* |
| *S. chartarum* (P&K 0184) | +* |
| Stachybotrys sp. (HRC/UNLV 1) | + |
| Stachybotrys sp. (HRC/UNLV 2) | + |
| Stachybotrys sp. (HRC/UNLV 3) | + |
| Stachybotrys sp. (HRC/UNLV 4) | +* |
| Stachybotrys sp. (HRC/UNLV 5) | + |
| Stachybotrys sp. (HRC/UNLV 6) | +* |
| Stachybotrys sp. (HRC/UNLV 7) | +* |
| *Stachybotrys dichroa* (ATCC 18917) | – |
| *Stachybotrys microspora* (ATCC 18852) | – |
| *Stachybotrys nephrospora* (ATCC 22706) | – |
| *Acremonium strictum* (ATCC 10141) | – |
| *Alternaria alternata* (ATCC 6663) | – |
| *Aspergillus niger* (ATCC 10535) | – |
| *Aspergillus versicolor* | – |
| Beauveria sp. | – |
| Bipolaris sp. | – |
| Chaetomium sp. | – |

TABLE 2-continued

PCR results obtained for the specificity testing of *Stachybotrys chartarum* primers STAF1 and STAR1.

| Organism | PCR results |
|---|---|
| *Cladosporium herbarum* (ATCC 28987) | – |
| *Fusarium oxysporum* (ATCC 48112) | – |
| *Memnoniella echinata* (ATCC 32888) | – |
| *Memnoniella subsimplex* (ATCC 22700) | – |
| *Penicillium chrysogenum* (ATCC 9480) | – |
| *Penicillium expansum* (ATCC 7861) | – |
| Phoma sp. | – |
| Rhizopus sp. | – |
| Trichoderma sp. | – |
| Ustilago sp. | – |
| Verticillium sp. | – |

+, amplification;
–, no amplification;
*, results following sample dilution;
ATCC, American Type Culture Collection;
P&K, P&K Microbiology Services, Cherry Hill, NJ;
HRC/UNLV, Harry Reid Center for Environmental Studies, University of Nevada-Las Vegas.

All fungal extracts tested for the presence of DNA with the dot quantitation method produced positive results (data not shown) with one exception. The *Aspergillus niger* DNA sample, which contained a black pigment, did not emit fluorescence under U.V. transillumination; however, a tenfold dilution of this sample produced positive results.

Enumeration of crude spore suspensions using the Coulter Multisizer II produced a large peak between 2.5 and 9.0 μm (particle diameter) corresponding to *S. chartarum* spores and a secondary peak smaller than 2 μm corresponding to debris, probably spore and hyphal fragments. Adjusting the spore counts to the appropriate size range of Stachybotrys spores was not sufficient for the preparation of PCR quantitation standards because the smaller particulate fraction produced positive PCR results when amplified with the *S. chartarum* primers (data not shown). Filtration of spore suspensions through mixed cellulose ester, polycarbonate, and teflon membranes did not remove the debris. Sucrose density centrifugation was effective in cleaning the spore suspension by separating the particles in the spore-size range from those 2 μm in diameter and smaller. The effectiveness of this methodology for the removal of the smaller particulate present in the supernatant was assessed by enumeration with the Coulter Multisizer. Therefore, this method was utilized for cleaning the spore suspensions prior to the preparation of PCR quantitation standards.

DNA Extraction and Purification

Two *S. chartarum* spore suspensions (ATCC 9182 and HRC/UNLV 1) were subjected to boiling or bead beating protocols for the extraction of DNA. Bead beating and boiling produced comparable amplification with undiluted samples (data not shown). Boiling was selected as the DNA extraction protocol based on sensitivity, removal of PCR inhibitors, and ease of use. Following extraction of fungal DNA, several Stachybotrys sp. isolates required further purification for the removal of PCR inhibitors. Table 3 summarizes the purification methods tested for this purpose. After testing a series of commercially available purification kits, two methods were selected. The boiling protocol followed by Pellet Paint and QiaPlant (DNeasy Plant Kit) was selected due to its sensitivity. The boiling protocol followed by purification through genomic tips (QIAGEN Genomic tip 20/G) in conjunction with the Genomic DNA Buffer set was the most effective in the removal of PCR inhibitors; however, the efficiency of recovery of DNA was low (Table 3).

TABLE 3

DNA concentration and purification methods tested for the detection of *Stachybotrys chartarum* in pure culture using QPCR.

| | | | QPCR result (Ct value) | | |
|---|---|---|---|---|---|
| Purification method | Strain | Conc. | Undiluted | $10^{-1}$ | $10^{-2}$ |
| Boil/Pellet Paint[a]/QIAamp[b] | ATCC | $10^4$ | 39.9 | Neg | Neg |
| | HRC 1 | $10^5$ | Neg | Neg | Neg |
| Boil/QiaPlant[c]/Pellet Paint | ATCC | $10^5$ | 30.3 | 30.4 | 35.0 |
| | HRC 1 | $10^5$ | Neg | 32.3 | 35.4 |
| Boil/Dynabeads[d] | ATCC | $10^5$ | 37.6 | Neg | Neg |
| | HRC 1 | $10^5$ | Neg | Neg | Neg |
| Boil/Pellet Paint/QiaPlant | ATCC | $10^4$ | 27.4 | nd | nd |
| | HRC 1 | $10^4$ | 28.6 | nd | nd |
| | P&K 0180 | $10^5$ | Neg | Neg | 35.2 |
| | P&K 0062 | $10^5$ | Neg | 31.5 | 32.9 |
| Boil/Pellet Paint/QiaPlant/Tip[e] | P&K 0180 | $10^5$ | Neg | 34.3 | 38.7 |
| | P&K 0062 | $10^5$ | 31.6 | 32.6 | 36.8 |
| Boil/Pellet Paint/Tip | P&K 0180 | $10^5$ | Neg | 37.8 | 39.1 |
| | P&K 0062 | $10^5$ | Neg | 34.6 | 37.5 |
| Boil/Tip | P&K 0180 | $10^5$ | 36.6 | 39.2 | Neg |
| | P&K 0062 | $10^4$ | 35.8 | 38.1 | Neg |

Ct values represent the mean of two replicates. Concentration refers to the theoretical amount of template subjected to amplification in the PCR reaction. Undiluted, $10^{-1}$ and $10^{-2}$ represent dilutions of DNA subjected to PCR amplification.
ATCC strain, American Type Culture Collection strain 9182;
HRC, Harry Reid Center for Environmental Studies;
P&K, P&K Microbiological Services;
Neg, Ct value of 40;
nd, not done.
[a]Pellet Paint Co-Precipitant
[b]QIAamp Blood and Tissue Kit.
[c]Dneasy Plant kit.
[d]Dynabeads
[e]QIAGEN Genomic tip 20/G The efficiency of removal of PCR inhibitors was dependent on the volume of sample extracted. Negative PCR results were obtained for 500 μl aliquots of *S. chartarum* spores (ATCC 9182 and HRC/UNLV 1) extracted by bead beating followed by Elu-Quik ($10^7$ spores, data not shown) and in $10^{-1}$ and $10^{-2}$ dilutions of the DNA post-extraction. PCR results were also negative for the 500 μl aliquots of the *S. chartarum* laboratory isolates (HRC/UNLV 6 and P&K 0177) extracted by the boiling/Pellet Paint/QiaPlant protocol and in the $10^{-1}$ DNA dilution samples but positive for the $10^{-2}$ DNA dilution (Table 4). Only one dilution was necessary to obtain positive PCR results when the spore sample volume was reduced to 100 μl for extraction through the boiling/Pellet Paint/QiaPlant protocol. No dilutions were necessary to obtain positive PCR results when purifying the same volume with the Elu-Quik protocol; however, the efficiency of recovery of DNA was low with this protocol compared with the other methods. All 10 μl spore aliquots amplified without further dilution of the DNA regardless of the purification method used.

TABLE 4

Comparison of DNA purification methods for the removal of PCR inhibitors and the effect of sample volume on the detection of *Stachybotrys chartarum* using QPCR.

| Extraction protocol | Strain | Vol. | QPCR result (Ct value) Undiluted | $10^{-1}$ | $10^{-2}$ |
|---|---|---|---|---|---|
| Boil/Pellet Paint[a]/ Elu-Quik[b] | HRC 6 | 10 μl | 38.1 | nd | nd |
| | | 100 μl | 34.9 | 37.0 | Neg |
| | | 500 μl | nd | nd | nd |
| | P&K 0177 | 10 μl | 37.1 | nd | nd |
| | | 100 μl | 34.8 | 36.8 | Neg |
| | | 500 μl | nd | nd | nd |
| Boil/Pellet Paint/ QiaPlant[c] | HRC 6 | 10 μl | 33.3 | nd | nd |
| | | 100 μl | Neg | 33.5 | 36.6 |
| | | 500 μl | Neg | 39.8 | 34.3 |
| | P&K 0177 | 10 μl | 31.7 | nd | nd |
| | | 100 μl | Neg | 32.5 | 35.1 |
| | | 500 μl | Neg | Neg | 34.0 |

Ct values represent the mean of two replicates. Volume refers to the amount of sample used for DNA extraction. Undiluted, $10^{-1}$ and $10^{-2}$ represent dilutions of DNA subjected to PCR amplification.
HRC, Harry Reid Center for Environmental Studies;
P&K, P&K Microbiological Services;
Neg = Ct value of 40;
nd, not done.
[a]Pellet Paint Co-Precipitant
[b]Elu-Quik DNA Purification Kit.
[c]DNeasy Plant kit.

PCR Inhibition

An internal positive control (IPC) produced a Ct of 26 (Table 5) when amplified alone but a higher Ct when PCR inhibitors were present. A previously amplified *S. chartarum* sample (P&K 0175) produced negative PCR results when undiluted and positive results when diluted. Amplification of this DNA using the IPC produced negative results of both the sample and the internal positive control when undiluted, indicating total inhibition. Partial inhibition of the IPC was observed in the $10^{-1}$ dilution, indicating that fewer inhibitors were present in the diluted sample.

TABLE 5

PCR results of inhibited *Stachybotrys chartarum* samples amplified with an internal positive control (IPC).

| Sample | Dilution | PCR results (Ct value) Sample | | IPC | |
|---|---|---|---|---|---|
| P&K 0175 | $10^0$ | 40.00 | 40.00 | 40.00 | 40.00 |
| | $10^{-1}$ | 36.16 | 37.19 | 27.41 | 27.66 |
| | $10^{-2}$ | 33.28 | 32.56 | 26.28 | 25.97 |
| P&K 0180 | $10^0$ | 38.45 | 38.51 | 26.19 | 26.55 |
| P&K 0062 | $10^0$ | 38.52 | 38.12 | 26.34 | 26.12 |
| Positive control | | 24.99 | 25.11 | 26.12 | 26.08 |
| Negative control | | 40.00 | 40.00 | 25.91 | 26.02 |
| No amplification control | | 40.00 | 40.00 | 40.00 | 40.00 |

Ct values represent replicates of the same sample. The positive control contained purified *S. chartarum* control DNA, and the negative control contained sterile water instead of DNA.
The no amplification control contained no target DNA, IPC DNA and a blocking reagent to prevent amplification of IPC DNA (Ct of 40 = negative result).

No inhibition of the IPC (Ct=26) was observed in the $10^{-2}$ dilution of the sample. Two other samples (P&K 0180 and P&K 0062) that had previously produced negative PCR results were re-extracted and purified with the QIAGEN Genomic tip 20/G (Table 3). Amplification of these samples using the IPC produced positive results of the sample when undiluted and Cts of 26 for the internal positive control, indicating the absence of inhibition (Table 5).

PCR Quantitation Standards

*Stachybotrys chartarum* quantitation standards ($10^0$ to $10^5$) were prepared from clean spore suspensions (ATCC 9182 and HRC/UNLV1) enumerated with the Coulter Multisizer II in order to quantitate *S. chartarum* by PCR. The DNA from standards of known concentration was extracted by the boiling/Pellet Paint/QiaPlant protocol developed. The ATCC and HRC/UNLV standards prepared were amplified and compared in order to select the best set of standards based on correlation coefficient of the regression analysis of the standard curve. The laboratory strain produced a more linear standard curve with a correlation coefficient ($r^2$) of 0.996. QPCR sensitivity using these standards was <23 template copies per PCR reaction. Laboratory *S. chartarum* isolates (HRC/UNLV 1, HRC/UNLV 4, P&K 0060, and P&K 0180) enumerated with the Coulter Multisizer II and quantitated with the 7700 SDS showed similar enumeration by the two methods (Table 6). The ATCC and one laboratory isolate (P&K 0062) had lower quantitation with the 7700 SDS than with the Coulter Multisizer II. In the case of the environmental isolate, the difference was probably due to inhibitors still present in the sample producing an artificially high Ct value and therefore, a lower quantitation with QPCR than anticipated. Serial dilution of several environmental samples produced amplification results corresponding to equivalent quantitation between electronic counts and QPCR (data not shown). The discrepancy in quantitation with the ATCC strain could not be explained by the presence of inhibitors.

TABLE 6

QPCR results obtained for *Stachybotrys chartarum* samples enumerated with the Coulter Multisizer II and quantitated with the 7700 Sequence Detection System.

| Sample | Dilution | Ct value | 7700 quantitation (template/ml) | Coulter enumeration (spores/ml) |
|---|---|---|---|---|
| HRC 1 [a] | $10^0$ | 23.5 | $1.08 \times 10^9$ | $5.69 \times 10^8$ |
| HRC 1 [b] | $10^0$ | 25.8 | $2.22 \times 10^8$ | $4.66 \times 10^8$ |
| ATCC | $10^0$ | 32.3 | $2.27 \times 10^6$ | $2.08 \times 10^8$ |
| P&K 0060 | $10^0$ | 40.0 | 0 | $4.58 \times 10^6$ |
|  | $10^{-2}$ | 34.5 | $4.02 \times 10^6$ |  |

TABLE 6-continued

QPCR results obtained for *Stachybotrys chartarum* samples enumerated with the Coulter Multisizer II and quantitated with the 7700 Sequence Detection System.

| Sample | Dilution | Ct value | 7700 quantitation (template/ml) | Coulter enumeration (spores/ml) |
|---|---|---|---|---|
| P&K 0062 | $10^0$ | 40.0 | 0 | $3.47 \times 10^6$ |
|  | $10^{-2}$ | 36.0 | $6.10 \times 10^5$ |  |
| P&K 0180 | $10^0$ | 40.0 | 0 | $6.11 \times 10^6$ |
|  | $10^{-2}$ | 34.9 | $3.15 \times 10^6$ |  |
| HRC 4 | $10^0$ | 40.0 | 0 | $3.56 \times 10^6$ |
|  | $10^{-2}$ | 35.3 | $2.27 \times 10^6$ |  |

ATCC and laboratory *S. chartarum* isolates were sampled and the DNA was extracted and purified with the developed protocol in order to test the efficiency of the quantitation standards prepared.
Ct values represent the mean of two replicates. (Ct of 40 = negative result). Undiluted and $10^{-2}$ represent dilutions of DNA subjected to PCR amplification.
HRC, Harry Reid Center for Environmental Studies;
ATCC strain, American Type Culture Collection strain 9182;
P&K, P&K Microbiological Services.
[a,b] Two different spore harvests of strain HRC/UNLV 1

CONCLUSION

Methods consistent with the present invention, therefore, enable the detection and absolute quantitation of *S. chartarum* using QPCR. By employing oligonucleotide primer sequences to amplify *S. chartarum* quantitation standards in parallel with unknown samples, an amplification curve can be constructed from which the concentrations of *S. chartarum* in the unknown samples may be interpolated.

The foregoing description of exemplary embodiments of the present invention provides illustration and description, but is not intended to be exhaustive or to limit the invention to the precise form disclosed. Modifications and variations are possible in light of the above teachings or may be acquired from practice of the invention. Also, while series of steps have been described with regard to FIGS. 1–7, the order of the steps may not be critical.

No element, act, or instruction used in the description of the present application should be construed as critical or essential to the invention unless explicitly described as such. Also, as used herein, the article "a" is intended to include one or more items. Where only one item is intended, the term "one" or similar language is used. The scope of the invention is defined by the following claims and their equivalents.

What is claimed is:

1. A method for detecting the fungus *Stachybotrys chartarum*, comprising:
   isolating DNA from a sample suspected of containing the fungus *Stachybotrys chartarum*;
   subjecting the DNA to polymerase chain reaction amplification utilizing at least one primer, wherein the at least one primer comprises one of a (SEQ ID NO: 1) 5'GTTGCTTCGGCGGGAAC3' and (SEQ ID NO: 2) 5'TTTGCGTTTGCCACTCAGAG3' base sequence; and
   detecting the fungus *Stachybotrys chartarum* by visualizing the product of the polymerase chain reaction.

2. The method of claim 1, wherein subjecting the DNA to polymerase chain reaction further utilizes a probe comprising a base sequence (SEQ ID NO: 5) 6-FAM-5'CTGCGCCCGGATCCAGGC3'-TAMRA.

3. A primer set for detecting *Stachybotrys chartarum* using polymerase chain reaction, comprising:
   a first primer comprising a base sequence (SEQ ID NO: 1) 5'GTTGCTTCGGCGGGAAC3'; and
   a second primer comprising a base sequence (SEQ ID NO:2) 5'TTTGCGTTTGCCACTCAGAG3'.

4. The primer set of claim 3, wherein the first primer comprises a forward primer.

5. The primer set of claim 3, wherein the second primer comprises a reverse primer.

6. A primer set for detecting *Stachybotrys chartarum* using polymerase chain reaction, comprising:
   a first primer comprising a first base sequence (SEQ ID NO: 3) 5'ACCTATCGTTGCTTCGGCG3'; and
   a second primer comprising a second base sequence (SEQ ID NO: 4) 5'GCGTTTGCCACTCAGAGAATACT3'.

7. The primer set of claim 6, wherein the first primer comprises a forward primer.

8. The primer set of claim 6, wherein the second primer comprises a reverse primer.

9. A primer and probe set for detecting the fungus *Stachybotrys chartarum* using polymerase chain reaction, comprising:
- a forward primer comprising a base sequence (SEQ ID NO: 1) 5'GTTGCTTCGGCGGGAAC3';
- a reverse primer comprising a base sequence (SEQ ID NO: 2) 5'TTTGCGTTTGCCACTCAGAG3'; and
- a probe comprising a base sequence (SEQ. ID NO. 5) 6-FAM-5CTGCGCCCGGATCCAGGC3'-TAMRA.

10. A primer and probe set for detecting the fungus *Stachybotrys chartarum* using polymerase chain reaction, comprising:
- a forward primer comprising a first base sequence (SEQ ID NO: 3) 5'ACCTATCGTTGCTTCGGCG3';
- a reverse primer comprising a second base sequence (SEQ ID NO: 4) 5'GCGTTTGCCACTCAGAGAATACT3'; and
- a probe comprising a base sequence (SEQ ID NO: 5) 6-FAM-5'CTGCGCCCGGATCCAGGC3'-TAMRA.

11. A primer for use in polymerase chain reaction, comprising:
- a base sequence comprising at least one of a first, second, third and fourth base sequence,
- wherein the first base sequence comprises (SEQ ID NO: 1) 5'GTTGCTTCGGCGGGAAC3',
- wherein the second base sequence comprises (SEQ ID NO: 2) 5'TTTGCGTTTGCCACTCAGAG3',
- wherein the third base sequence comprises (SEQ ID NO: 3) 5'ACCTATCGTTGCTTCGGCG3', and
- wherein the fourth base sequence comprises (SEQ ID NO: 4) 5'GCGTTTGCCACTCAGAGMTACT3'.

12. A method for detecting the presence of the fungus *Stachybotrys chartarum*, comprising:
- obtaining a sample from the environment;
- extracting DNA from the sample; and
- amplifying the extracted DNA by polymerase chain reaction utilizing one or more primers to obtain an indication of the presence of *Stachybotrys chartarum* in the sample, wherein the one or more primers comprise at least one of a (SEQ ID NO: 1) 5'GTTGCTTCGGCGGGAAC3'and (SEQ ID NO: 2) 5'TTTGCGTTTGCCACTCAGAG3'base sequence.

13. The method of claim 12, wherein amplifying the sample by polymerase chain reaction further utilizes a probe comprising a base sequence (SEQ ID NO: 5) 6-FAM-5'CTGCGCCCGGATCCAGGC3'-TAMARA.

14. A method for detecting the presence of the fungus *Stachybotrys chartarum*, comprising:
- obtaining a sample from the environment;
- extracting DNA from the sample; and
- amplifying the extracted DNA by polymerase chain reaction utilizing a primer set to obtain an indication of the presence of *Stachybotrys chartarum* in the sample, wherein the primer set comprises:
  - a forward primer comprising a base sequence (SEQ ID NO: 1) 5'GTTGCTTCGGCGGGAAC3', and
  - a reverse primer comprising a base sequence (SEQ ID NO: 2) 5'TTTGCGTTTGCCACTCAGAG3'.

15. The method of claim 14, wherein amplifying the sample by polymerase chain reaction further utilizes a probe comprising a base sequence (SEQ ID NO: 5) 6-FAM-5'CTGCGCCCGGATCCAGGC3'-TAMRA.

16. A method for detecting the presence of the fungus *Stachybotrys chartarum*, comprising:
- obtaining a sample from the environment;
- extracting DNA from the sample; and
- amplifying the extracted DNA by polymerase chain reaction utilizing a primer set to obtain an indication of the presence of *Stachybotrys chartarum* in the sample, wherein the primer set comprises:
  - a forward primer comprising a first base sequence (SEQ ID NO: 3) 5'ACCTATCGTTGCTTCGGCG3', and
  - a reverse primer comprising a second base sequence (SEQ ID NO: 4) 5'GCGTTTGCCACTCAGAGAATACT3'.

17. The method of claim 16, wherein amplifying the sample by polymerase chain reaction further utilizes a probe comprising a base sequence (SEQ ID NO: 5) 6-FAM-5'CTGCGCCCGGATCCAGGC3'-TAMRA.

* * * * *

SEQUENCE LISTING

<160> NUMBER OF SEQ ID NOS: 5

<210> SEQ ID NO 1
<211> LENGTH: 17
<212> TYPE: DNA
<213> ORGANISM: Stachybotrys chartarum
<220> FEATURE:
<221> NAME/KEY:
<222> LOCATION:
<223> OTHER INFORMATION:

<400> SEQUENCE: 1
gttgcttcgg cgggaac

```
<210> SEQ ID NO 2
<211> LENGTH: 20
<212> TYPE: DNA
<213> ORGANISM: Stachybotrys chartarum
<220> FEATURE:
<221> NAME/KEY:
<222> LOCATION:
<223> OTHER INFORMATION:

<400> SEQUENCE: 2
tttgcgtttg ccactcagag                                           20

<210> SEQ ID NO 3
<211> LENGTH: 19
<212> TYPE: DNA
<213> ORGANISM: Stachybotrys chartarum
<220> FEATURE:
<221> NAME/KEY:
<222> LOCATION:
<223> OTHER INFORMATION:

<400> SEQUENCE: 3
acctatcgtt gcttcggcg                                            19

<210> SEQ ID NO 4
<211> LENGTH: 23
<212> TYPE: DNA
<213> ORGANISM: Stachybotrys chartarum
<220> FEATURE:
<221> NAME/KEY:
<222> LOCATION:
<223> OTHER INFORMATION:

<400> SEQUENCE: 4
gcgtttgcca ctcagagaat act                                       23

<210> SEQ ID NO 5
<211> LENGTH: 18
<212> TYPE: DNA
<213> ORGANISM: Stachybotrys chartarum
<220> FEATURE:
<221> NAME/KEY:
<222> LOCATION:
<223> OTHER INFORMATION:

<400> SEQUENCE: 5
ctgcgcccgg atccaggc                                             18
```